US007294177B2

(12) United States Patent
Shimomura

(10) Patent No.: US 7,294,177 B2
(45) Date of Patent: Nov. 13, 2007

(54) GAS CHROMATOGRAPH MASS SPECTROMETER

(75) Inventor: Manabu Shimomura, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 306 days.

(21) Appl. No.: 11/087,666

(22) Filed: Mar. 24, 2005

(65) Prior Publication Data

US 2005/0211098 A1    Sep. 29, 2005

(30) Foreign Application Priority Data

Mar. 26, 2004    (JP)    ............................. 2004-090869

(51) Int. Cl.
*B01D 53/02* (2006.01)
(52) U.S. Cl. ...................... 96/106; 73/23.37
(58) Field of Classification Search ................ 96/101, 96/104, 105, 106, 107; 95/82, 85, 86, 87, 95/88; 73/23.35, 23.37, 23.39, 23.4, 23.42
See application file for complete search history.

(56) References Cited

U.S. PATENT DOCUMENTS

| 4,641,541 | A | * | 2/1987 | Sharp | ........................ | 73/23.37 |
| 6,247,731 | B1 | | 6/2001 | Stearns et al. | | |
| 2006/0123883 | A1 | * | 6/2006 | Miyagawa | .................. | 73/23.37 |

FOREIGN PATENT DOCUMENTS

| JP | 10-283982 | 10/1998 |
| JP | 2001-208740 | 8/2001 |
| WO | WO 01/73338 A1 | 10/2001 |

OTHER PUBLICATIONS

Nyholm et al., "High-temperature open tubular liquid chromatography coupled to atmospheric pressure chemical ionization mass spectrometry"; Journal of Chromatography A, Elsevier, Amsterdam. NL, vol. 755, No. 2, Dec. 6, 1996, pp. 153-164, XP004014701.

* cited by examiner

*Primary Examiner*—Duane Smith
*Assistant Examiner*—Robert A Clemente
(74) *Attorney, Agent, or Firm*—Westerman, Hattori, Daniels & Adrian, LLP.

(57) ABSTRACT

An interface placed between a gas chromatograph part and a mass spectrometer part of a gas chromatograph mass spectrometer for allowing one or two columns to pass air-tightly from the gas chromatograph part to the mass spectrometer part. The interface includes: a heat-retention block having a small-diameter hole allowing two columns to pass through; a single-hole ferrule having a small-diameter hole allowing a single column to pass through; and a two-hole ferrule having two small-diameter holes allowing two columns to respectively pass through. An adapter is placed between the heat-retention block and the two-column nut. It includes a long large-diameter opening allowing two columns passing through the two-hole ferrule to converge on the small-diameter hole of the heat-retention block. The interface also includes a single-column nut for pressing the single-hole ferrule to the heat-retention block; and a two-column nut for pressing the two-hole ferrule to the adapter.

5 Claims, 3 Drawing Sheets

Fig. 1A
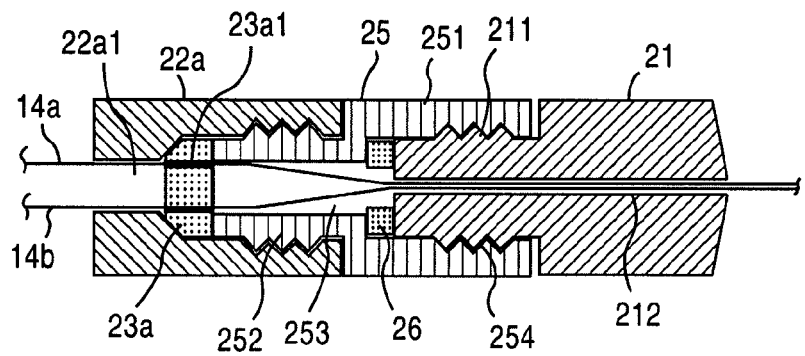
Fig. 1B
Fig. 1C
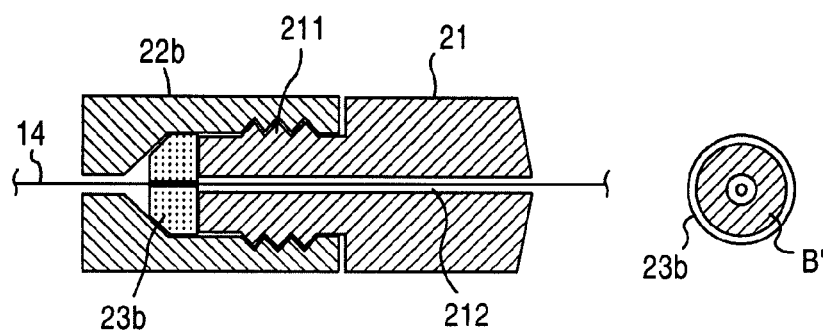
Fig. 2
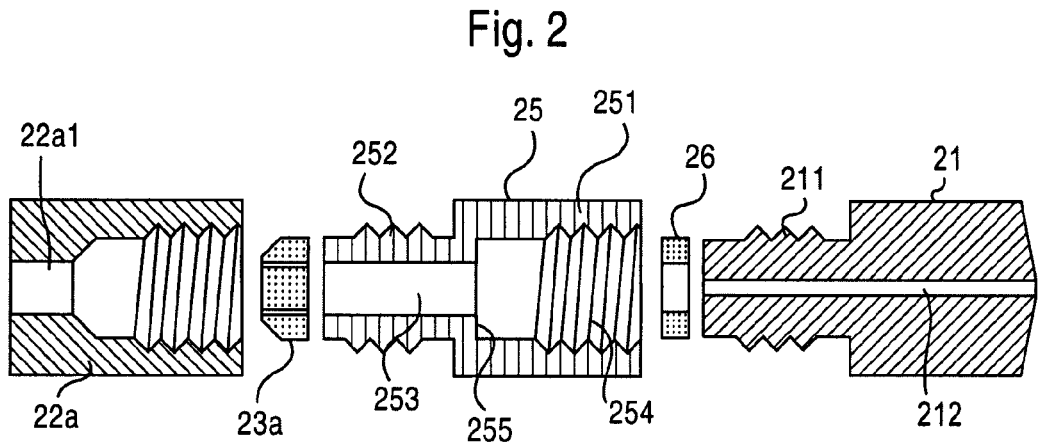

GAS CHROMATOGRAPH MASS SPECTROMETER

The present invention relates to a gas chromatograph mass spectrometer in which a mass spectrometer is used as a detector of a gas chromatograph, and specifically to an interface which connects the gas chromatograph part and the mass spectrometer part.

BACKGROUND OF THE INVENTION

Gas chromatograph mass spectrometers (GC/MS) are nowadays widely used in qualitative as well as quantitative analyses of various sample substances. A conventional gas chromatograph mass spectrometer is described referring to FIG. 3. The Unexamined Japanese Patent Publication Nos. H10(1998)-283982 and 2001-208740 disclose such gas chromatograph mass spectrometers.

In a gas chromatograph (GC) part 10, a sample atomizer 11 is provided at the entrance of a capillary column 14, which is enclosed by a column oven 13. A carrier gas flows through the sample atomizer 11 and the column 14 at a constant rate. When a liquid sample is injected by an injector 12 into the sample atomizer 11, the sample is instantaneously atomized and is carried by the carrier gas to the column 14. The column 14 is heated by the column oven 13 at a predetermined temperature so that components contained in the sample are separated with respect to time while the sample passes through the column 14. The sample gas, including the separated components, is introduced via an interface 20 to an ionizing chamber 31 of a mass spectrometer (MS) part 30. The mass spectrometer part 30 is housed in a vacuum chamber 35 which is evacuated by a pump. The sample molecules are ionized in the ionizing chamber 31, where various ionizing methods can be used including the electron impact (EI) ionization method. Ions thus generated are drawn out of the ionizing chamber 31, converged by an ion lens 32, and introduced to a quadrupole mass filter 33. A combination of a DC voltage and an AC voltage is applied to the quadrupole mass filter 33, and ions having a specific mass to charge ratio corresponding to the applied voltage can pass the quadrupole mass filter 33, and are detected by an ion detector 34.

The primary purpose of the interface 20 connecting the GC part 10 and the MS part 30 is to maintain the temperature at about the exit of the column 14 at almost the same as that inside the column oven 13, whereby the sample gas is constantly introduced into the ionizing chamber 31 without disruption. The interface 20 thus contains a heater unit.

In the GC part 10 of a GC/MS, various columns having different selectivity characteristics are used depending on the object and kind of the sample to be analyzed. Thus an exchange of columns is often necessary, which is one of troublesome operations of a GC/MS.

In a type of GC/MS with sample atomizers 11a, 11b, two (or more) columns 14a, 14b are provided in the column oven 13 as shown in FIG. 4, and an appropriate one of the two columns 14a, 14b is used according to the object of the analysis and the sample. In such a type of GC/MS, the exits of the two columns 14a, 14b are merged with a T-joint 15, and the merged column 16 is extended to the ionizing chamber 31 via the interface 20. In such a type, however, the gas pressure in the T-joint 15 is influenced by those in the two columns 14a and 14b, so that the calculation of the carrier gas flow, which is determined by the pressures at the entrance and at the exit of a column, becomes complicated and less precise.

The above problem can be solved by extending the two columns 14a and 14b in parallel to the ionizing chamber 31 via the interface 20, rather than joining them before the interface 20. Since, in this method, the exits of the two columns 14a and 14b are in a vacuum, the flow of the carrier gas can be calculated precisely as in the case of a single column.

The above construction has a drawback as follows. As shown in FIG. 5, the interface 20 includes a tubular heat-retention metal block 21 whose end is made into a threaded bolt 211. A metal nut 22 is screwed into the bolt 211 with a plastic ferrule 23 between them. The column 14 is inserted in a small central hole 231 of the plastic ferrule 23. As the nut 22 is screwed into the bolt 211 of the heat-retention block 21 to a certain strength, the plastic ferrule 23 is pressed to the end of the bolt 211 and its central hole 231 tightly holds the column 14. Since the central hole 212 of the heat-retention block 21 opens to the ionizing chamber 31 as shown in FIG. 3, the inside of the central hole 212 is also in a vacuum. Since the ferrule 23 seals around the column 14, gas is prevented from leaking from the GC part 10 into the MS part 30.

In the case of two columns 14a and 14b extending in parallel to the ionizing chamber 31, the construction of the interface 20 shown in FIG. 5 becomes as shown in FIGS. 6A and 6B. Since the two columns 14a and 14b should be separated by a certain distance in the column oven 13, a ferrule 23a having two small holes 23a1 separated by the distance, as shown in FIGS. 6A and 6B, is used. Correspondingly, the nut 22a must have a central opening 22a1 larger than the outer distance A of the two holes 23a1 of the ferrule 23a, and the heat-retention block 21a must have a central opening 21a2 larger than the outer distance A.

Using such an interface 20, it is possible to use two columns 14a and 14b in the gas chromatograph part 10 of the GC/MS. But, in many cases, only a single column is used with such a two-column interface. In this case, the one-column nut 22b and one-hole ferrule 23b as shown in FIG. 6C are used instead of those shown in FIG. 6A.

There is a problem in this case. Since the central opening 21a2 of the heat-retention block 21a is large, the contact area B between an end of the heat-retention block 21 and that of the ferrule 23b is rather small as shown in FIG. 6D, which weakens the air seal effect. The problem can be avoided by using the proper heat-retention block 21 for a single column, or by changing the whole interface to the one-column interface 20 as shown in FIG. 5. But the changing operation of the interface 20 needs a lot of care and is time-consuming. Preparing two sets of interfaces is also financially disadvantageous.

SUMMARY OF THE INVENTION

In view of the above-described problems, the present invention provides a gas chromatograph mass spectrometer that can be used with a single column and with a multiple column as desired without changing the whole interface, whereas, when using with a single column, which quite often occurs, the mass spectrometer part can be kept in a good vacuum.

Thus the present invention provides an interface placed between a gas chromatograph part and a mass spectrometer part of a gas chromatograph mass spectrometer (GC/MS) for allowing a column or a plurality of columns to pass airtightly from the gas chromatograph part to the mass spectrometer part. According to the present invention, the interface includes:

a heat-retention block having a small-diameter hole for allowing the plurality of columns to pass therethrough;

a single-hole ferrule having a small-diameter hole for allowing a single column to pass therethrough;

a plural-hole ferrule having a plurality of small-diameter holes for allowing the plurality of columns to respectively pass therethrough;

an adapter placed between the heat-retention block and the below-described plural-column nut, and including a long large-diameter opening for allowing the plurality of columns passing through the plural-hole ferrule to converge on the small-diameter hole of the heat-retention block without excessively bending the plurality of columns;

a single-column nut for pressing the single-hole ferrule to the heat-retention block; and a plural-column nut for pressing the plural-hole ferrule to the adapter.

The interface of the present invention is used as follows. When a single column is used in the gas chromatograph part, the heat-retention block, the single-hole ferrule and the single-column nut are used. In this case, the heat-retention block and the ferrule contact with a large area, which ensures a high air-tightness. When a plurality of columns are used in the gas chromatograph part, the heat-retention block, the adapter, the plural-hole ferrule and the plural-column nut are used. The plurality of columns passing through the plurality of small-diameter holes respectively of the plural-hole ferrule can converge on the small-diameter hole of the heat-retention block without being excessively bent or forced owing to the long large-diameter opening of the adapter. The change of the two modes is rather easy, and the difference in the two cases is the change of the ferrules and nuts, and insertion of the adapter, which are all relatively inexpensive. The expensive heat-retention block is commonly used, and the high vacuum of the MS part is assured by the small-diameter hole of the heat-retention block in both cases.

BRIEF DESCRIPTION OF THE DRAWINGS

FIG. 1A is a longitudinal sectional view of an interface for two columns used in an embodiment of the present invention, FIG. 1B is the same for one-column, and FIG. 1C is the cross-sectional view of the ferrule and bolt of the heat-retention block in the case of one-column (FIG. 1B).

FIG. 2 is a separated sectional view of the two-column interface shown in FIG. 1A.

DETAILED DESCRIPTION OF A PREFERRED EMBODIMENT

Figure 3:
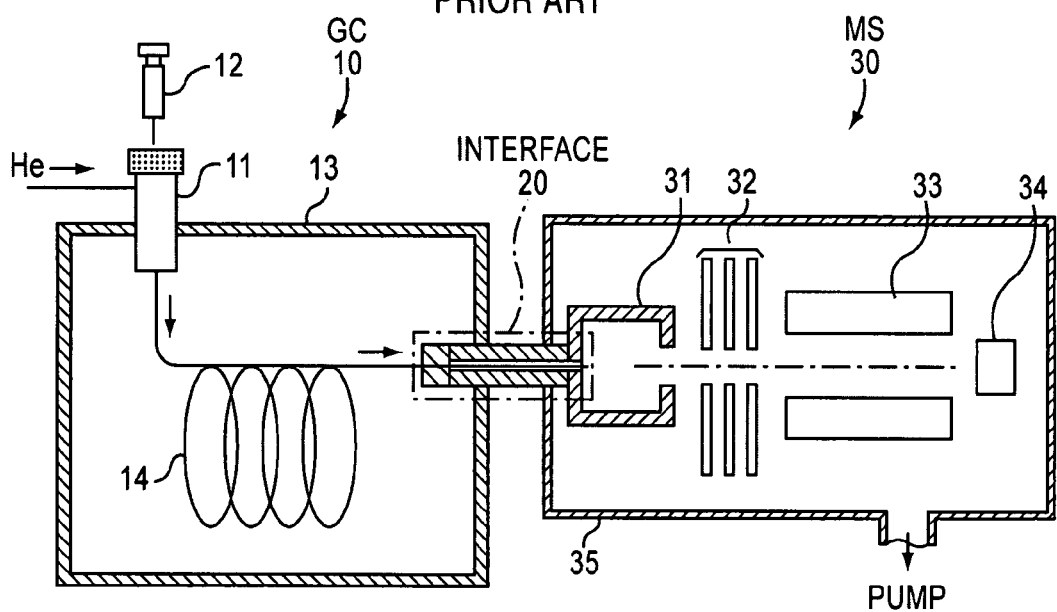
FIG. 3 is a sectional view of a general gas chromatograph mass spectrometer (GC/MS).

A GC/MS embodying the present invention is described referring to the attached drawings. The principal structure of the GC/MS of the present embodiment is as shown in FIG. 3 and as described above, whereas the GC/MS of the present embodiment has a characteristic structure in the interface 20.

The structure of the interface 20 of the GC/MS of the present embodiment is described referring to FIGS. 1A, 1B, 1C and 2.

Figure 4:
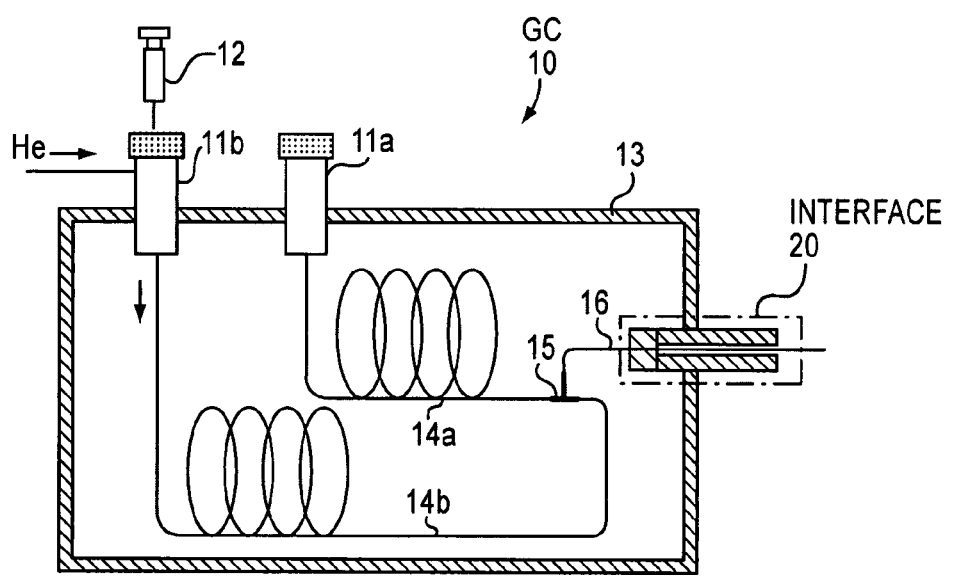
FIG. 4 is a sectional view of the gas chromatograph part of the GC/MS in which two columns are used.
Figure 5:
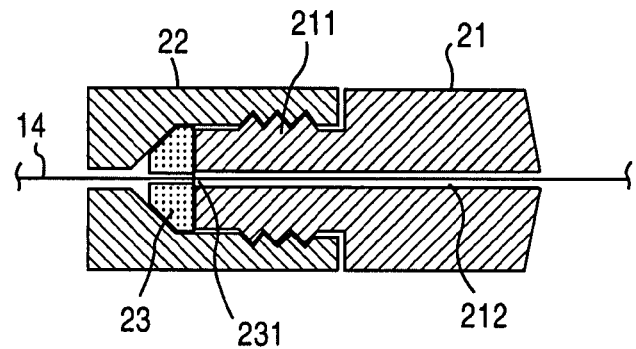
FIG. 5 is a longitudinal sectional view of a conventional interface.
Figure 6A:
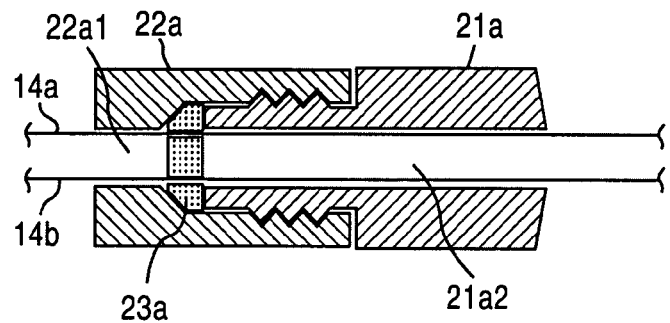
FIG. 6A is a longitudinal sectional view of a conventional interface used with two columns.
Figure 6B:
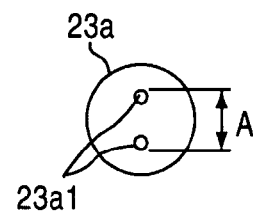
FIG. 6B is its cross-sectional view.
Figure 6C:
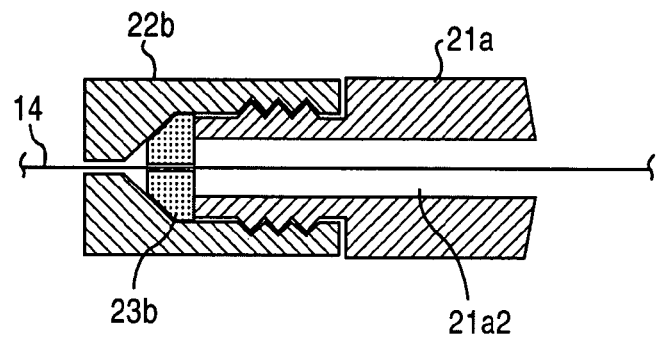
FIG. 6C is a longitudinal sectional view of another conventional interface used with a single column.
Figure 6D:
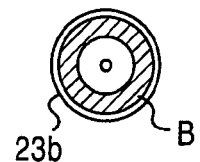
FIG. 6D is its cross-sectional view.

FIG. 1A shows the interface 20 of the present embodiment when used with two columns, and FIG. 1B shows the same when used with a single column. FIG. 2 shows the components of the interface 20 as used with two columns (FIG. 1A) in a separated state. The elements as described above are assigned the same numbers as those in said figures. The diameter of the hole 212 of the heat-retention block 21 is the same as that shown in FIG. 4, so that two columns 14a, 14b can pass the hole 212 in a close position. When the interface 20 is used with a single column 14, as shown in FIG. 1B, the single-hole ferrule 23b made of plastic and a corresponding nut 22b are used. In this case, the ferrule 23b and the heat-retention block 21 make greater contact with each other, as shown by B' in FIG. 1C, which ensures a high air-tightness.

When two columns 14a and 14b are to be extended to the ionizing chamber 31, as shown in FIG. 1A, an adapter 25 and the two-hole plastic ferrule 23a are inserted between the heat-retention block 21 and a two-column nut 22a. The adapter 25 is made of metal, such as a stainless steel, and is composed of a larger end 251 and a smaller end 252. The larger end 251 has a threaded larger opening 254 in which the bolt 211 of the heat-retention block 21 is screwed, and the smaller end 252 has an outer screw adaptable to the nut 22a. In the smaller end 252, a smaller opening 253 is created whose diameter is larger than the distance A between the outer ends of the two small holes 23a1 of the ferrule 23a. The smaller opening 253 connects with the larger opening 254 with a step 255 between them.

When the bolt 211 of the heat-retention block 21 is screwed into the larger opening 254 of the adapter 25, a ring seal 26 is inserted between them. As the bolt 211 is tightened into the adapter 25, the seal 26 is pressed against the step 255 and changes shape so that the bolt 211 and the larger opening 254 are air-tightened.

When the smaller end 252 of the adapter 25 is screwed into the nut 22a, the two-hole ferrule 23a is inserted between them. As the adapter 25 is tightened into the nut 22a, the ferrule 23a changes shape so that the adapter 25 and the nut 22a are air-tightened, and the two columns 14a, 14b are air-tightly pressed by the respective small holes 23a1 of the ferrule 23a. Since a long space (the "long large-diameter opening" described above) is provided by the smaller opening 253 of the adapter 25, the two columns 14a, 14b passing through the small holes 23a1 of the ferrule 23a can converge, without being excessively bent or forced, on the small central hole 212 of the heat-retention block 21.

Although only some exemplary embodiments of the present invention have been described in detail above, those skilled in the art will readily appreciate that many modifications are possible without materially departing from the present invention. Accordingly, all such modifications are intended to be included within the scope of the present invention. For example, it is possible in the case of a single column to use the two-column nut 22a shown in FIG. 1A, instead of the single-column nut 22b shown in FIG. 1B, though the column 14 may be slightly unstable.

What is claimed is:

1. An interface placed between a gas chromatograph part and a mass spectrometer part of a gas chromatograph mass spectrometer (GC/MS) for allowing a column or a plurality of columns to pass air-tightly from the gas chromatograph part to the mass spectrometer part, the interface comprising:

a heat-retention block having a small-diameter hole for allowing the plurality of columns to pass therethrough;

a single-hole ferrule having a small-diameter hole for allowing a single column to pass therethrough;

a plural-hole ferrule having a plurality of small-diameter holes for allowing the plurality of columns to respectively pass therethrough;

an adapter placed between the heat-retention block and the below-described plural-column nut, and including a long large-diameter opening for allowing the plurality of columns passing through the plural-hole ferrule to converge on the small-diameter hole of the heat-retention block without excessively bending the plurality of columns;

a single-column nut for pressing the single-hole ferrule to the heat-retention block; and a plural-column nut for pressing the plural-hole ferrule to the adapter.

2. The GC/MS interface according to claim 1, wherein the adapter is composed of a larger end and a smaller end, where the larger end has a larger opening adaptable to the heat-retention block, and the smaller is adaptable to the nut.

3. The GC/MS interface according to claim 1, wherein the interface further comprises a ring ferrule inserted between the adapter and the heat-retention block for keeping the adapter and the heat-retention block air-tight.

4. The GC/MS interface according to claim 1, wherein the single-hole ferrule and the plural-hole ferrule are made of plastic.

5. The GC/MS interface according to claim 1, wherein the number of the plurality is two.

* * * * *